(12) United States Patent
Frith

(10) Patent No.: US 7,387,605 B2
(45) Date of Patent: Jun. 17, 2008

(54) ROTATABLE COUPLER FOR ENDOSCOPIC CAMERA

(75) Inventor: Martin A. Frith, Goleta, CA (US)

(73) Assignee: Linvatec Corporation, Largo, FL (US)

( * ) Notice: Subject to any disclaimer, the term of this patent is extended or adjusted under 35 U.S.C. 154(b) by 650 days.

(21) Appl. No.: 11/102,898

(22) Filed: Apr. 8, 2005

(65) Prior Publication Data

US 2006/0229495 A1   Oct. 12, 2006

(51) Int. Cl.
*A61B 1/04* (2006.01)
(52) U.S. Cl. ........................................ 600/112; 600/137
(58) Field of Classification Search ............... 600/112, 600/133, 137; 359/827; 403/348, 322.1; 385/25
See application file for complete search history.

(56) References Cited

U.S. PATENT DOCUMENTS

| | | | | |
|---|---|---|---|---|
| 3,597,578 A | * | 8/1971 | Sullivan et al. | 219/121.67 |
| 4,303,300 A | * | 12/1981 | Pressiat et al. | 385/26 |
| 4,501,442 A | * | 2/1985 | Partus | 285/190 |
| 4,611,888 A | * | 9/1986 | Prenovitz et al. | 600/112 |
| 4,825,850 A | * | 5/1989 | Opie et al. | 600/122 |
| 4,898,447 A | * | 2/1990 | Kuhlmann | 385/25 |
| 4,963,728 A | * | 10/1990 | Hof et al. | 250/227.11 |
| 4,969,450 A | * | 11/1990 | Chinnock et al. | 600/109 |
| 5,156,141 A | * | 10/1992 | Krebs et al. | 600/112 |
| 6,428,470 B1 | * | 8/2002 | Thompson | 600/173 |
| 6,633,438 B2 | * | 10/2003 | Anhalt | 359/694 |
| 6,869,397 B2 | * | 3/2005 | Black et al. | 600/168 |
| 2004/0109164 A1 | * | 6/2004 | Horii et al. | 356/479 |

* cited by examiner

*Primary Examiner*—John P. Leubecker
(74) *Attorney, Agent, or Firm*—Gene Warzecha

(57) ABSTRACT

A rotatable endoscope coupler which enables an endoscope to be rotatably attached to a camera and selectively locked in place. The coupler enables single handed rotation of the scope while the camera remains in a fixed orientation. A plurality of ceramic ball bearings riding in a stainless steel race enable the coupler to be repeatedly autoclaved. A locking mechanism allows the scope and camera to be fixed from relative rotation.

10 Claims, 7 Drawing Sheets

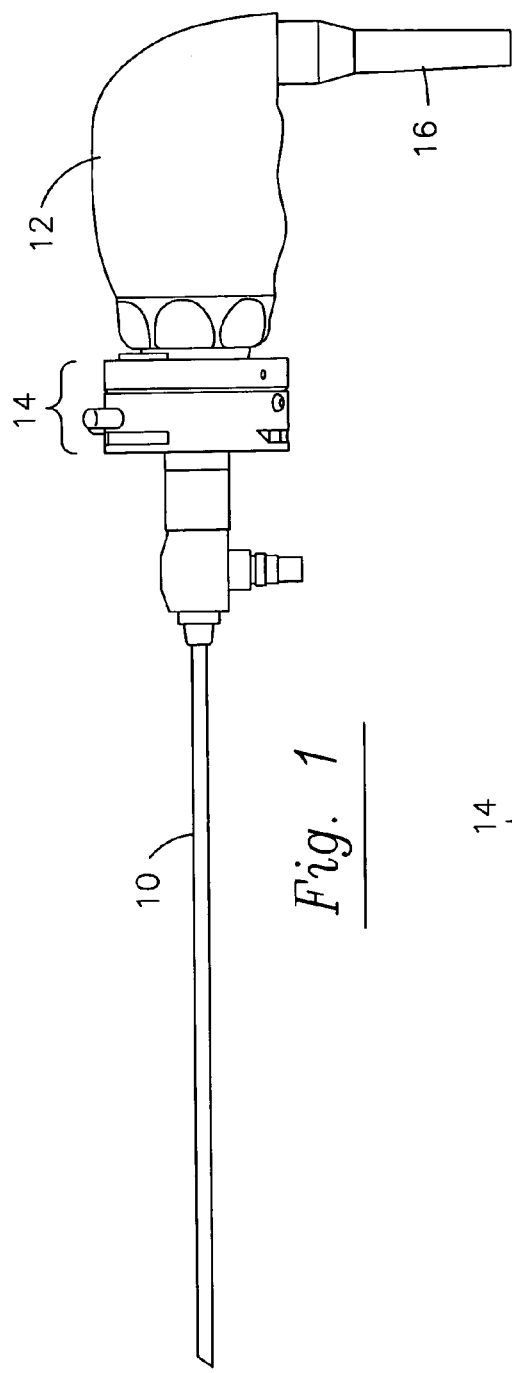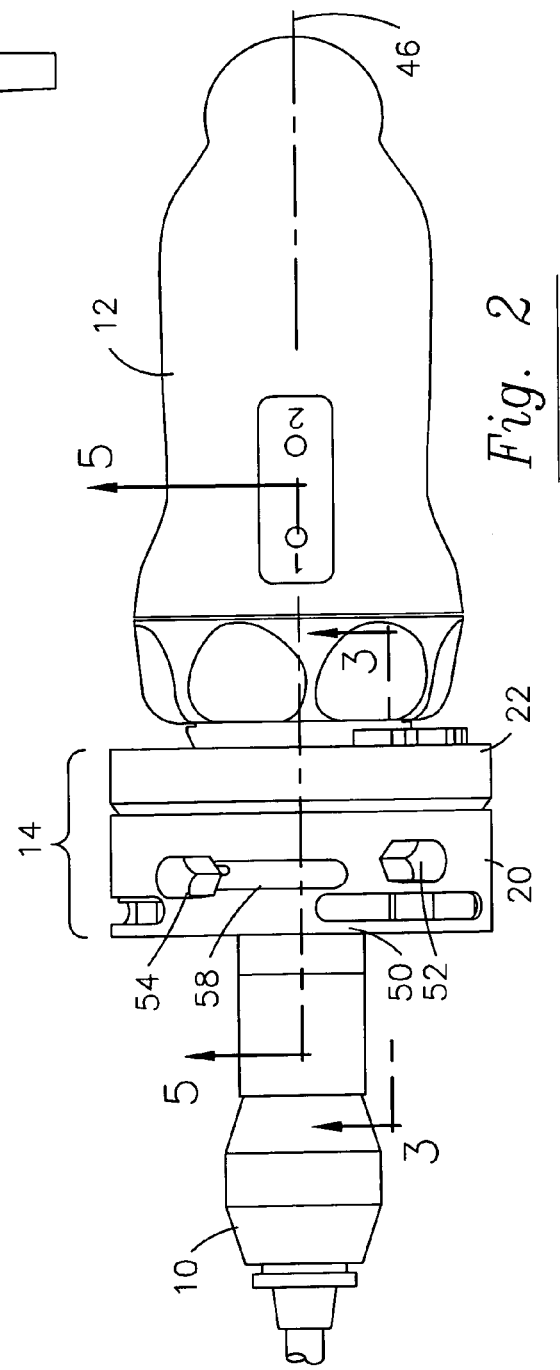

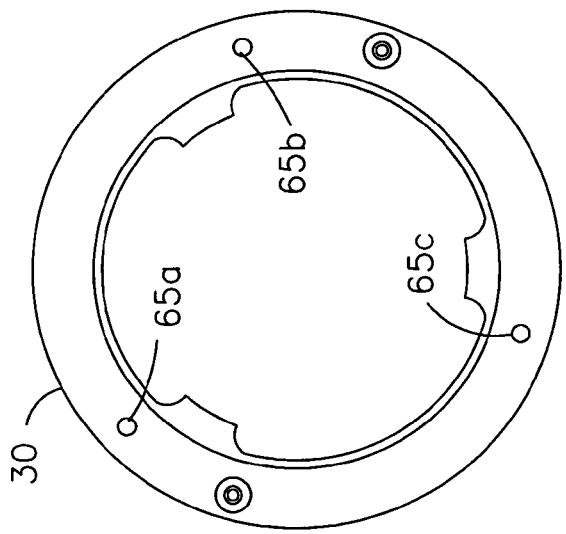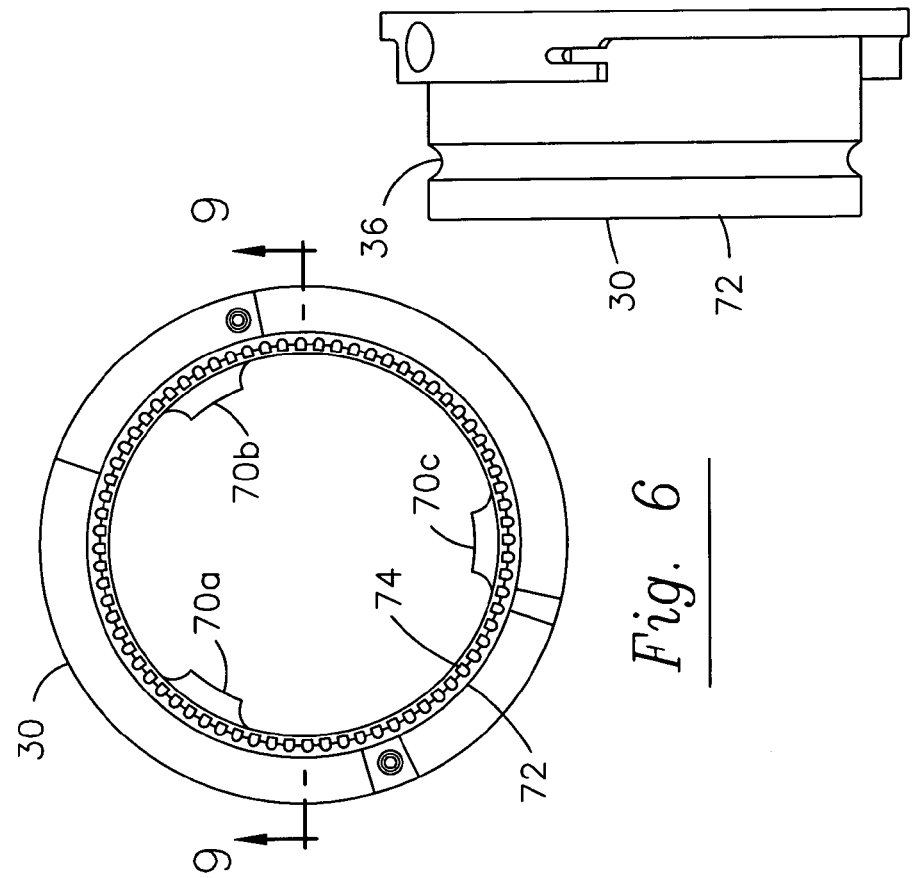

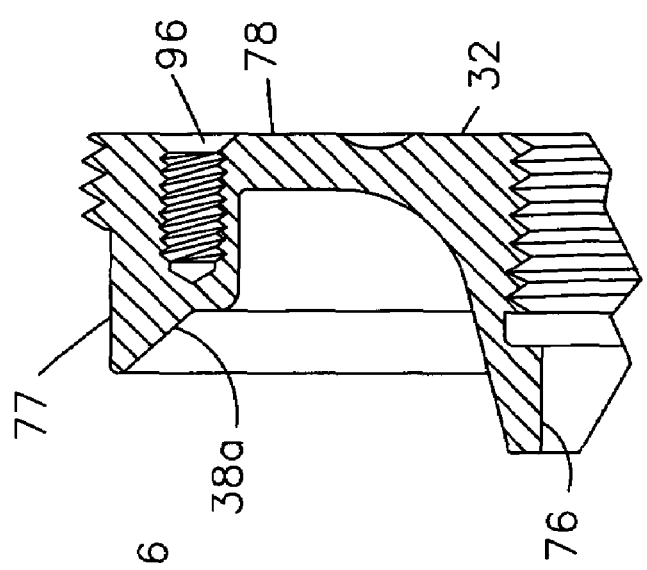
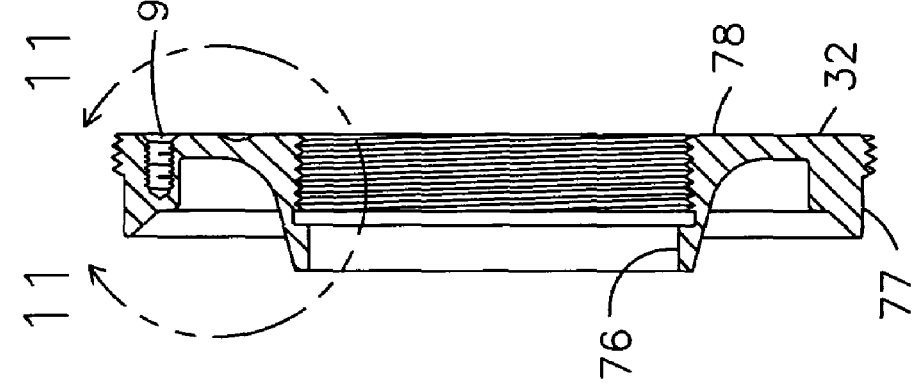
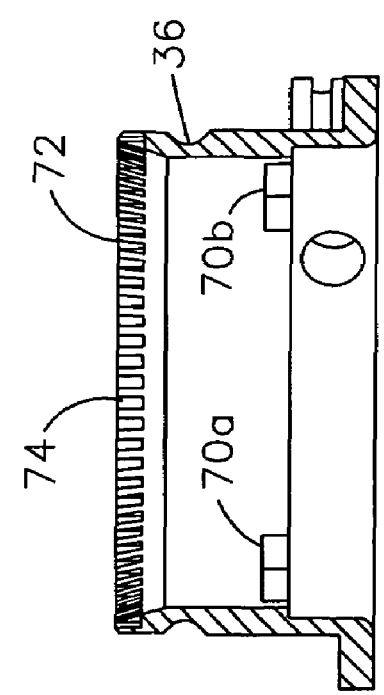

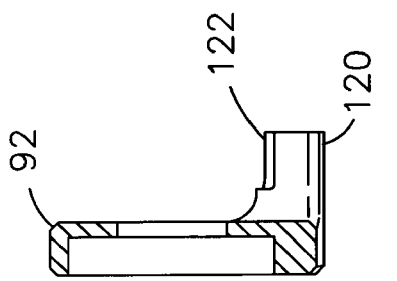
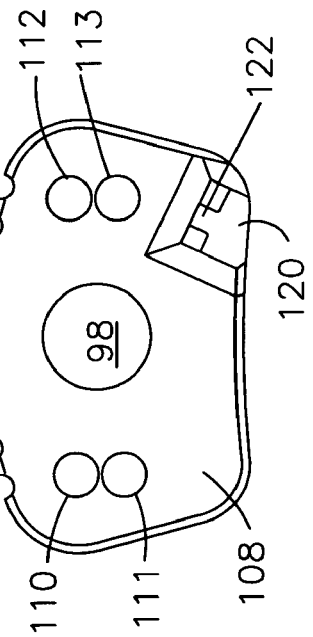
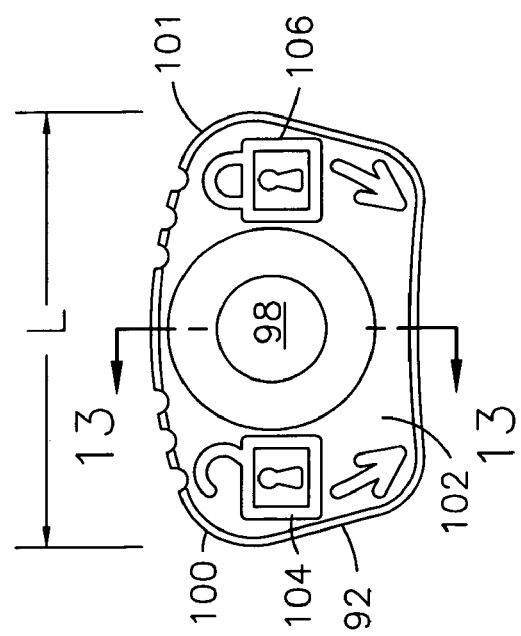

ROTATABLE COUPLER FOR ENDOSCOPIC CAMERA

BACKGROUND OF THE INVENTION

1. Field of the Invention

The present invention pertains to endoscope couplers for optically and mechanically coupling an endoscope to a video camera. More particularly, the invention relates to endoscope couplers which enable relative rotation of the endoscope and camera about the endoscope axis.

2. Description of the Prior Art

Endoscopes have become widely utilized in surgery for viewing body cavities and organs to permit performance of diagnostic and surgical procedures internally without the need for invasive surgical procedures. An endoscope is typically inserted through a small incision or portal or natural body passage to provide access to the body cavity. A lens at a distal end of the endoscope is positioned to receive light reflected from a site to be observed, and images of the site can be viewed remotely to conduct diagnostic examinations and to perform closed, or endoscopic surgery. As used herein, the term endoscope refers generically to viewing devices for remotely observing otherwise inaccessible body cavities with minimal trauma and intrusion, including but not limited to arthroscopes, colonoscopes, bronchoscopes, hysteroscopes, cystoscopes, sigmoido-scopes, laparoscopes and ureterscopes, etc.

Endoscopes are sometimes supplied with an eyepiece at the proximal end thereof, and relay lenses in the endoscope typically produce an image for direct viewing through the eyepiece. However, adaptation of video camera technology to endoscopy imaging has enabled the output image of an endoscope to be viewed on a video monitor. Specifically, a video camera is electronically coupled to the video monitor and optically and mechanically coupled with the proximal end of the endoscope. Indirect or video monitor viewing of endoscopic images provides numerous benefits over direct viewing through an eyepiece, including: protection of a direct viewer's vision from high intensity illumination passed through the endoscope and reflecting off bodily tissue; enhancement of operator comfort and freedom of movement; increased endoscope utility and efficiency; reduction in the time required to conduct many endoscopic procedures; simultaneous viewing of endoscopic images by more than one person; and recordation and real time transmission of images of surgical procedures.

An endoscope coupler is required to couple the proximal end of the endoscope to the video camera and may be made as a separate device or in combination with either the endoscope or the video camera or both. Illustrative endoscope couplers are shown in U.S. Pat. No. 4,569,333 (Bel et al.); U.S. Pat. No. 4,611,888 (Prenovitz et al.); U.S. Pat. No. 4,740,058 (Hori et al.); U.S. Pat. No. 4,781,448 (Chatenever et al.); U.S. Pat. No. 4,807,594 (Chatenever); U.S. Pat. No. 4,844,071 (Chen et al.); U.S. Pat. No. 4,969,450 (Chinnock et al.); U.S. Pat. No. 5,056,902 (Chinnock et al.) and U.S. Pat. No. 5,359,992 (Hori et al.). Endoscope couplers sometimes include a cylindrical body which may be closed at opposing ends by end windows and contain a lens holder carrying one or more lenses longitudinally movable within the body to optically adjust an image from the endoscope onto a focal plane of the camera. The optical adjustments most commonly used may be a focus and/or zoom adjustment. Sometimes, endoscope couplers operate with the eyepiece of an endoscope and other times the eyepiece is replaced with an optical arrangement which must be viewed through the camera and monitor (that is, no eyepiece is available).

In addition to enabling optical adjustments, in certain applications such as the urology field, it is often necessary to maintain the camera in a fixed position while rotating the endoscope about its axis in order to view the surgical site. Therefore, rotatable endoscopic couplers have been developed to enable this rotation of the scope relative to the camera. Such couplers may not include any optical components although they serve to properly position the proximal end of the scope relative to the distal end of the camera so the image planes are properly spaced along their common axis. Known rotatable endoscopic couplers generally include a distal ring, which may be fixedly attached to the proximal end of the endoscope, a proximal ring, which may be fixedly attached to a camera, and a rotatable interface between the two rings. The rotatable interface often includes a plain bearing structure (not ball bearings) and a selectively actuatable lock (such as a lever with a pin or cam) to selectively prevent rotation.

Additionally, it is advantageous for the surgeon to use only one hand to manipulate the scope or the camera thereby leaving the other hand free to operate various instruments during surgical procedures. Therefore, rotatable couplers must be easy to operate.

Aforementioned U.S. Pat. No. 4,969,450 (Chinnock et al.) discloses a rotatable coupler for a video arthroscope which can be held and controlled with one hand. The rotatability is achieved by closely fitting cylindrical members including bores and counterbores which are rotatable about their common axes and sealed with several O-rings.

Another example of a rotatable coupler is shown in U.S. Pat. No. 4,611,888 (Prenovitz et al.). The Prenovitz coupler consists of two sections rotatable with respect to one another, the front section being non-rotatably mounted to the proximal end of an arthroscope and the rear section being non-rotatably mounted to the distal end of a video camera. The image produced by the scope is rotatable relative to the camera by simply rotating the front section relative to the rear section.

In order to maintain sterile surgical conditions, all imaging components, including endoscope couplers, whether rotatable or not, must be sterilized before and after each use. Steam autoclaving has long been the best accepted method of sterilization and is used for all instruments that can withstand the necessary high temperature and pressure. Instruments that will not survive the steam autoclave process, such as video cameras and prior art endoscopic couplers are treated by less effective or less efficient means such as immersion in sterilization liquid or gas sterilization. However, there is no known conventional rotatable endoscopic coupler which can withstand repeated steam or other sterilization and all known rotatable endoscopic couplers are adversely affected by such.

While known prior art couplers are available to enable the rotation of the endoscopic image relative to the camera, all known rotatable couplers utilize bearing surfaces, which are rotatable relative to each other, and locking mechanisms in the form of cams and pins to frictionally engage the rotatable elements to lock them together when the desired angular orientation is achieved. Over time, these known rotatable coupler designs become more and more difficult to operate because of the build up of residue caused by improper cleaning as well as the deterioration of the cooperating parts caused by their exposure to the harsh environments of autoclaves. This deterioration eventually leads to the inability to easily operate the rotatable coupler with one hand and eventually leads to the inability to rotate the coupler at all. These prior art couplers must then be totally rebuilt or replaced.

An improved rotatable coupler design is necessary in order to enable the autoclavability of rotatable endoscopic couplers and improve their performance over an extended period of time.

It is, therefore, an object of this invention to produce a rotatable endoscope coupler for joining an endoscope to a camera.

It is also an object of this invention to provide a rotatable endoscope coupler capable of being repeatedly subjected to an autoclave without significant deterioration of performance.

It is still another object of this invention to produce a rotatable endoscope coupler incorporating ball bearings which are adapted to withstand the autoclave environment.

It is still another object of this invention to produce a rotatable endoscope coupler capable of being easily disassembled for repair.

It is also an object of the present invention to provide an endoscope coupler that may be quickly and easily inserted between an endoscope and a video camera or may be formed as an integral part of either the endoscope or the video camera or both.

SUMMARY OF THE INVENTION

These and other objects are accomplished by the preferred embodiment disclosed herein which is a rotatable coupler for coupling a camera to an optical assembly, preferably an endoscopic optical assembly. The coupler comprises a proximal camera attachment means for fixedly securing the coupler to a camera, a distal optical assembly attachment means for fixedly securing the coupler to an optical assembly and a selectively rotatable coupling means interposed between the camera attachment means and the optical assembly attachment means. In one embodiment, the rotatable coupling means comprises a first annular member which is fixedly connected to the optical assembly attachment means and a second annular member is fixedly secured to the camera attachment means. An annular ball bearing means is interposed between the first and second annular members to permit relative rotation therebetween. The first annular member has a plurality of radially inwardly directed slots and a locking means attached to the second annular member annular member is adapted to selectively engage the slots to lock the first annular member to the second annular member.

BRIEF DESCRIPTION OF THE DRAWINGS

FIG. 1 is a side elevational view of an endoscope, a camera and a rotatable coupler constructed in accordance with the principles of this invention.

FIG. 2 is a top plan view of a portion of FIG. 1.

FIG. 6 is a front elevational view of the first annular ring (element 30) shown in FIG. 4.

FIG. 7 is a side elevational view of FIG. 6.

FIG. 8 is a rear elevational view of FIG. 6.

FIG. 9 is a cross-sectional view of FIG. 6 taken along the line 9-9.

FIG. 10 is a cross-sectional view of the second annular ring (element 32) shown in FIG. 4.

FIG. 11 is an enlarged view of a portion of FIG. 10.

FIG. 12 is a front elevational view of the locking tab element 92 shown in FIG. 4.

FIG. 13 is a cross-sectional view of FIG. 12 taken along the line 13-13.

FIG. 14 is a rear elevational view of FIG. 12.

DESCRIPTION OF THE PREFERRED EMBODIMENT

FIGS. 1 and 2 show an endoscope 10 releasably connected to a camera head 12 via an intermediate rotatable coupler assembly 14 constructed in accordance with the principles of this invention.

Figure 3:
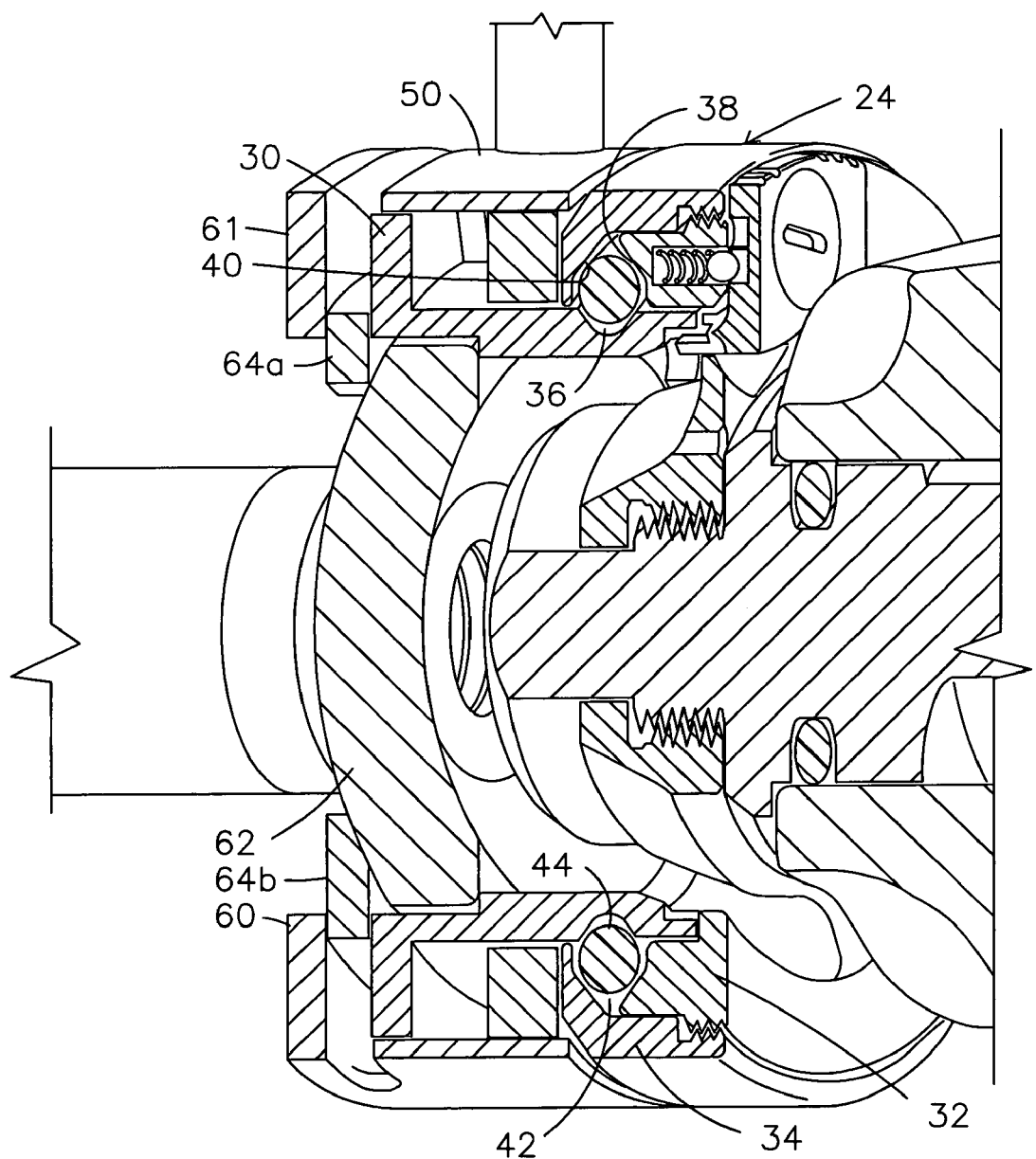
FIG. 3 is a cross-sectional perspective view taken generally along the line 3-3 of FIG. 2.

Coupler assembly 14 comprises a distal cylindrical "grabber" means 20, which is releasably attachable to the eyepiece of scope 10, and a proximal camera mount means 22 which, in the preferred embodiment is fixedly attached to camera 12. Grabber means 20 is selectively rotatable relative to camera mount means 22 by virtue of interface or bearing means 24 interposed therebetween, as best seen in FIG. 3. The freely rotatable grabber means enables a user to permit the camera head 12 (and, therefore, the monitor view) to remain fixed in selected orientation (e.g. upright), while rotating the scope about axis 46. Either the scope or the camera may be rotated about the axis with the fingers of the hand holding the camera head. For applications such as urology, for example, the surgeon need only grasp the scope thereby allowing the camera to orient itself vertically by virtue of the weight of power cord 16. Simply rotation of the scope about its axis will not affect the camera orientation. As will be explained below, for procedures requiring the scope and camera to be non-rotatable relative to each other, a locking feature is provided.

While the drawings are shown with an embodiment of the invention adapted to be used with an endoscope having an eyepiece, it will be understood that the invention could be adapted for use with any type of scope. The grabber means 20 may be replaced with an interface adapted to be affixed (permanently or removably) to the particular configuration of the proximal end of the scope to be coupled to the camera. Similarly, the rotatable coupler could be irremovably attached to the scope, or irremovably or removably attached to the camera, or removably or irremovably attachable to both.

Figure 4:
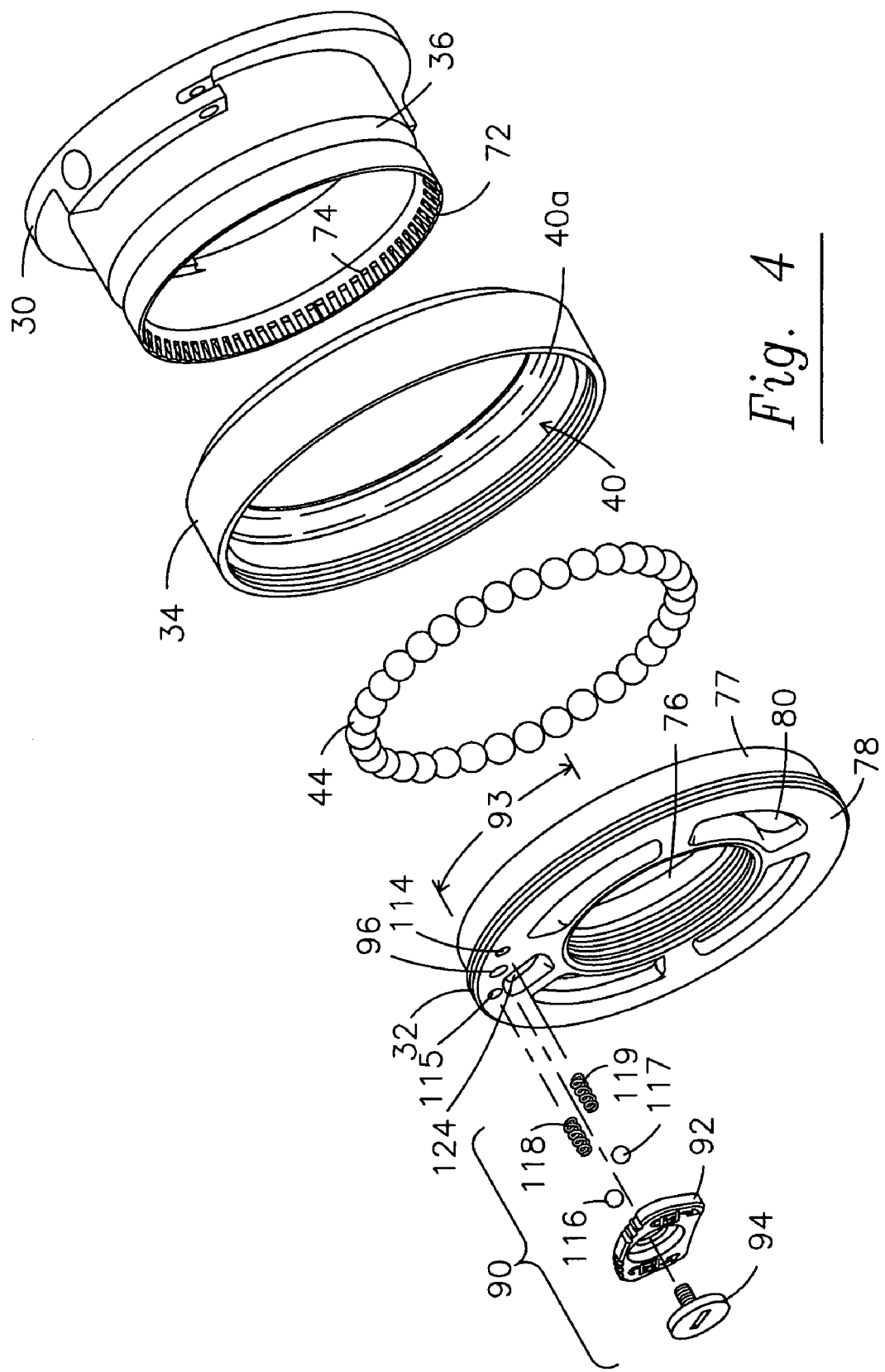
FIG. 4 is an exploded view of a portion of FIG. 3.
Figure 5:
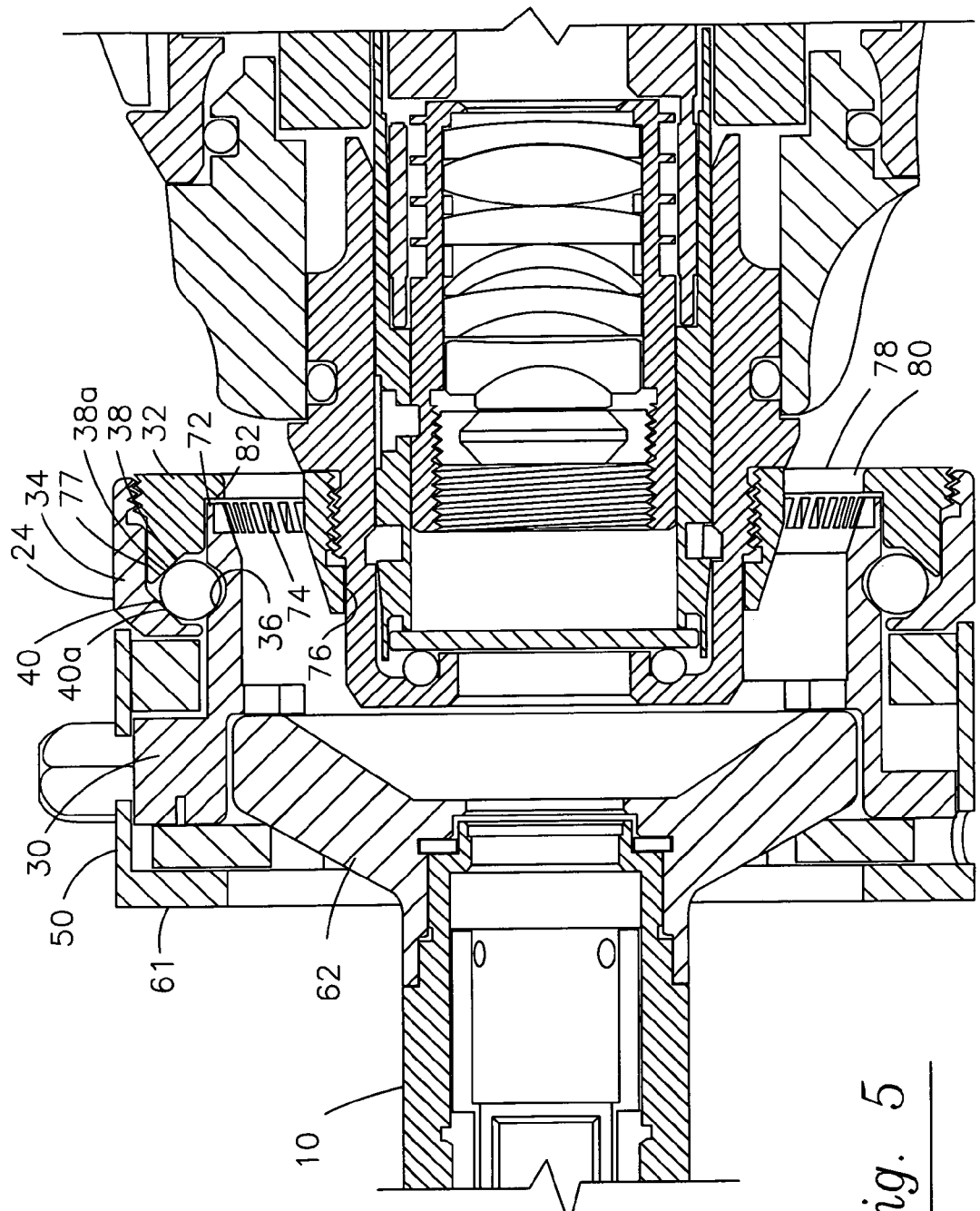
FIG. 5 is a cross-sectional view of FIG. 2 taken along the line 5-5.

As best seen in FIGS. 3 through 5, bearing means 24 comprises a distal, first annular ring 30 fixedly attached to grabber means 20, a proximally situated second annular ring 32 and a laterally situated, third annular ring 34. Annular rings 30, 32, 34 have cooperating surfaces 36, 38 and 40, respectively, which, when assembled, serve as a race 42 for a plurality of balls 44 circumferentially situated about the axis 46 of the coupler assembly 14. The assembly of the component parts of bearing means 24 may be understood by reference to the exploded view shown in FIG. 4.

It is noted that, in the preferred embodiment, race 42 is defined by three cooperating and threadably assembled stainless steel surfaces 36, 38 and 40 for ease of assembly and servicing. It will be understood that race 42 could be formed by more or fewer cooperating surfaces depending upon the design of the coupler, and could be assembled by means other than threads on rings 32 and 34. In the preferred embodiment there are thirty five balls 44, each made of ceramic and having a diameter of 0.125 inches. The ceramic material should be selected to withstand repeated sterilization cycles in an autoclave. However, should additional cleaning be required or should repairs or replacements be necessary, the rings 30, 32 and 34 may be easily disassembled. In the preferred embodiment surface 36 is an annular groove having a radius of curvature adapted to receive balls 44, and surfaces 38 and 40 each having planar annular portions 38a and 40a (best seen in FIG. 5).

Grabber means 20 has an outer cylindrical retaining member 50 that is provided with a fixed radial post 52. Another radial post 54 is secured to the distal, first annular ring 30. Retaining member 50 is secured to a spring member (not shown) interposed between the distal annular ring 30 and cylindrical member 50. Cylindrical member 50 is rotatable about axis 46 when a user squeezes posts 52 and 54 together because post 54 is able to move in arcuate slot 58. The circular opening 60 of flange 61 formed at the distal end of cylindrical member 50 has a diameter large enough to accept therethrough the eyepiece 62 of endoscope 10. Three arcuate and radially pivotable retaining arms 64a, 64b and 64c (the latter being hidden from view in FIG. 3) are pivotably attached to the distal surface of distal annular ring 30 at points 65a, 65b and 65c (best seen in FIG. 2). Each arm has a longitudinally extending pin (not shown) riding in a radially and laterally extending slot (not shown) in the distal flange 61 of cylindrical retaining member 50. As posts 52 and 54 are squeezed together, the relative rotation between the retaining member 50 and distal annular ring 30 causes the retaining arms to pivot about their attachment points to clear opening 60 to receive eyepiece 62. Releasing pressure on the posts 52 and 54 allows arms 64a, 64b and 64c to move radially inwardly behind the eyepiece to lock the eyepiece of the endoscope within the cylindrical retaining member 50. The arms, in cooperation with radially inwardly extending tabs 70a, 70b and 70c on distal ring 30 (best seen in FIG. 6) serve to position the eyepiece at the proper axial location relative to the optical components in camera 12. Once the scope is so situated, it may rotate about axis 46 along with the distal annular ring 30.

The proximal most rim 72 of annular ring 30 is provided with a plurality of radially inwardly extending slots 74. Slots 74 extend longitudinally and in the preferred embodiment are open and proximally facing at rim 72.

Proximally situated second annular ring 32 has an axially aligned opening 76 adapted to receive the distal end of camera 12. Opening 76 is threaded at its proximal end to receive a camera adapter or to receive a camera mount directly. Ring 32 has an outer cylindrical annular wall 77 and a transverse proximal wall 78, the latter provided with a plurality of circumferentially arranged ventilation apertures 80. Annular wall 77 has a length along axis 46 sufficient to properly place bearing race surface 38 relative to bearing surfaces 36 and 40 to define race 42 when the proximal ring 32 is threadably engaged with lateral ring 34. When fully assembled, the distally facing side 82 of proximal wall 78 will be adjacent to but spaced from the proximal most end of rim 72, and all surfaces 36, 38 and 40 will be contiguous with balls 44.

Second annular ring 32 carries a locking mechanism 90 which serves to prevent the relative rotation between the camera mount means 22 and the grabber means 20 by engaging a pivotable projection with the slots 74. Locking mechanism 90, best seen in FIGS. 4, 12, 13, and 14, comprises a toggle lever 92 pivotably secured to and adjacent the radially outer surface of the proximal side of ring 32 by a shoulder screw 94. Ring 32 has a screw-receiving threaded bore 96. Lever 92 is thus situated transversely to axis 46. The transverse length L of lever 92 is long enough so that when the lever is pivoted a predetermined amount clockwise or counterclockwise about its axis 98, one corner 100 or 101 will extend radially beyond the outer surface of annular ring 34. This enables one or the other corner of lever 92 to be easily pushed radially inwardly by the thumb (or other finger) of the hand holding the camera to toggle the lever from one extreme to the other, e.g. from locked to unlocked. Lever 92 is situated a predetermined arcuate lateral distance 93 from the top of the coupler to position it for easy accessibility.

The proximally facing surface 102 of lever 92 is provided with icons 104 and 106 (preferably molded, machined or otherwise form on the surface, or placed via a decal, paint, etc.) depicting a locked or unlocked condition and the direction in which the adjacent corner 100 or 101 must be pushed to achieve the desired condition.

The distally facing surface 108 of lever 92 is provided with a pair of detents 110 and 111, and a pair of detents 112 and 113. These detents are designed to cooperate with bores 114 and 115 formed in the proximally facing surface of ring 32, and with balls 116, 117 and springs 118, 119 to frictionally engage lever 92 and hold it in the locked or unlocked position. In the preferred embodiment balls 116 and 117 each have a diameter of 0.063 inches and are made of ceramic. (Balls 116, 117 and balls 44 are, in the preferred embodiment, also coated with a high temperature grease.) The distally facing surface 108 is also provided with a projection 120 extending distally and having an interference member or tooth 122. Proximal surface 78 of annular ring 32 is provided with an aperture 124 in order to receive projection 120 and tooth 122 therethrough and enable the tooth to be positioned radially inwardly of slots 74. When lever 92 is pivoted into a locked position, tooth 122 engages one of the slots 74, thus preventing relative rotation between the two sides of coupler 14.

It will be understood by those skilled in the art that numerous improvements and modifications may be made to the preferred embodiment of the invention disclosed herein without departing from the spirit and scope thereof.

What is claimed is:

1. A rotatable coupler for coupling a camera to an optical assembly comprising:
    a proximal camera attachment means for fixedly securing the coupler to a camera;
    a distal optical assembly attachment means for fixedly securing the coupler to an optical assembly;
    a selectively rotatable coupling means interposed between said camera attachment means and said optical assembly attachment means, said coupling means comprising:
    a first annular member having a plurality of radially inwardly directed slots, said first annular member fixedly connected to said optical assembly attachment means;
    a second annular member fixedly secured to said camera attachment means;
    ball bearing means interposed between said first and second annular members for permitting relative rotation therebetween; and
    locking means associated with said coupling means and adapted to selectively engage at least one of said slots to selectively lock or unlock said first annular member to said second annular member.

2. A rotatable coupler according to claim 1 wherein said optical assembly is an endoscope.

3. A rotatable coupler according to claim 1 wherein said slots are circumferentially situated at the proximal end of said first annular member.

4. A rotatable coupler according to claim 1 wherein said coupler, said camera and said optical assembly have a common axis, and wherein said locking means comprises:
   selectively engageable interference means attached to one of said first and second annular members for securing said first and second annular members together;
   means for moving said interference means into engagement with at least one of said slots.

5. A rotatable coupler according to claim 4 wherein said locking means further comprises:
   a toggle lever means pivotably secured to said second annular member, said toggle means pivotable about an axis parallel to said axis of said rotatable adapter between a first, released position and a second engaged position; and
   retaining means to hold said toggle lever means in a selected one of said positions.

6. A rotatable coupler according to claim 5 wherein said second annular member has an annular surface situated at a first predetermined radius and wherein said toggle lever, in each of said first and second positions, has a component thereof situated at a radius greater than said first predetermined radius.

7. In combination, an endoscopic camera, a rotatable coupler and an endoscope wherein said camera may be held in one hand with said endoscope situated distally of said camera and said rotatable coupler interposed between said camera and said endoscope, and wherein said rotatable coupler comprises:
   a distal member for being secured to said endoscope;
   a proximal member for being secured to said camera;
   a ball bearing means interposed between said proximal and distal members for enabling relative rotation therebetween; and
   a locking means for rotationally securing said proximal member to said distal member.

8. The combination of claim 7 wherein said locking means comprises an actuating member movable in a plane transverse to an axis of said coupler between a locked position and an unlocked position.

9. The combination of claim 7 wherein the combination is handheld and wherein said locking means is actuatable with a finger of the hand holding the combination.

10. The combination of claim 7 wherein said camera, said coupler and said endoscope are aligned along a common axis and therein said locking means is a toggle lever pivotable about an axis at a point situated a predetermined distance laterally relative to said axis.

* * * * *